United States Patent

Wroblowsky et al.

Patent Number: 5,606,070
Date of Patent: Feb. 25, 1997

[54] PROCESS FOR THE PREPARATION OF ALKOXYTRIAZOLINONES

[75] Inventors: Heinz-Jürgen Wroblowsky, Langenfeld; Klaus König, Odenthal; Joachim Kluth, Langenfeld; Klaus-Helmut Müller, Düsseldorf, all of Germany

[73] Assignee: Bayer Aktiengesellschaft, Leverkusen, Germany

[21] Appl. No.: 528,585

[22] Filed: Sep. 15, 1995

[30] Foreign Application Priority Data

Sep. 23, 1994 [DE] Germany .......................... 44 33 968.2

[51] Int. Cl.⁶ ............................................. C07D 249/12
[52] U.S. Cl. .......................................................... 548/263.6
[58] Field of Search ........................................... 548/263.6

[56] References Cited

U.S. PATENT DOCUMENTS 5,356,865  10/1994  Müller et al. .
5,488,028   1/1996  Haas et al. .............................. 504/193

FOREIGN PATENT DOCUMENTS 0507171  10/1992  European Pat. Off. .

OTHER PUBLICATIONS

P. R. Atkins, et al., J. Chem. Soc., Perkin I, pp. 2644–2646, (1973).
P. C. Guha, et al., J. Indian Chem. Soc., vol. 6, pp. 565–575, (1929).
Chemical Abstracts, vol. 42, abstract No. 8190d, abstract of Rev. Fac. Sci. Istanbul, vol. 13A, pp. 127–146, (1948).
Chemical Abstracts, vol. 108, abstract No. 56000r, p. 719, abstract of Arch. Pharm., vol. 320, pp. 608–616, (1988).
Chemical Abstracts, vol. 82, abstract No. 86060x, p. 494, abstract of Arch. Pharm., vol. 307, pp. 889–891, (1975).

*Primary Examiner*—Patricia L. Morris
*Attorney, Agent, or Firm*—Sprung Horn Kramer & Woods

[57] ABSTRACT

Alkoxytriazolinones of the general formula (I),

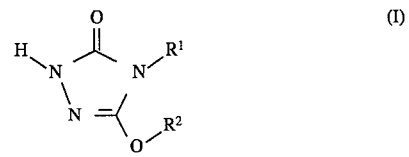

in which $R^1$ and $R^2$ independently of one another represent in each case optionally substituted alkyl, alkenyl, alkinyl, cycloalkyl, cycloalkylalkyl, aryl or arylalkyl, (which can be used as intermediates for the preparation of herbicidal active compounds) are obtained in very good yields and in high purity by reacting iminothiocarbonic diester (II) with carbazinic esters (III)

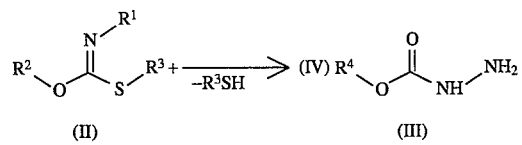

in which $R^3$ and $R^4$ in each case represent, for example, alkyl or aryl, at –20° C. to +50° C. (1st step) and subjecting the semicarbazide derivatives (IV) formed in this process with elimination of $R^3$–SH

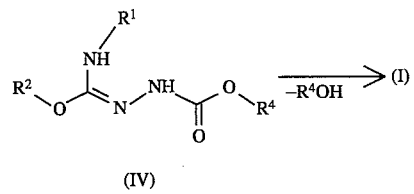

to a cyclizing condensation reaction and if appropriate in the presence of a base at 20° C. to 100° C. with elimination of $R^4$—OH, if appropriate after intermediate isolation (2nd step).

10 Claims, No Drawings

PROCESS FOR THE PREPARATION OF ALKOXYTRIAZOLINONES

The invention relates to a new process for the preparation of alkoxytriazolinones, most of which are known and which can be used as intermediates for the preparation of agrochemical active compounds, which can also be applied to an industrial-scale process.

Alkoxytriazolinones and a plurality of methods for their preparation are already known (cf. J. Indian Chem. Soc. 6 (1929), 565–575; J. Chem. Soc. Perkin I 1973, 2644–2646; Arch. Pharm. 307 (1974), 889–891; EP-A 477646; EP-A 507171). However, these known synthetic methods give alkoxytriazolinones only in highly unsatisfactory yields.

It is furthermore known to form 5-methoxy-4-methyl-2,4-dihydro-3H-1,2,4-triazol-3-one by methylating urazole or 4-methylurazole with diazomethane ($CH_2N_2$) [cf. F. Arndt et al, Rev. Fac. Sci. Istanbul 13A, pp. 127–144 (1948)]; while this method affords high yields of the triazolinone, it cannot be carried out on an industrial scale.

It has now been found that alkoxytriazolinones of the general formula (I)

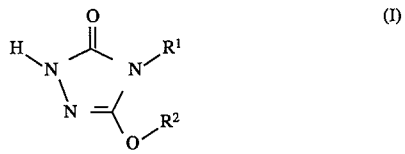

in which $R^1$ represents in each case optionally substituted alkyl, alkenyl, alkinyl, cycloalkyl, cycloalkylalkyl, aryl or arylalkyl and $R^2$ represents in each case optionally substituted alkyl, alkenyl, alkinyl, cycloalkyl, cycloalkylalkyl, aryl or arylalkyl, are obtained in very good yields and in high purity when iminothiocarbonic diesters of the general formula (II)

in which $R^1$ and $R^2$ have the abovementioned meanings and $R^3$ represents in each case optionally substituted alkyl, aryl or arylalkyl, are reacted with carbazinic esters of the general formula (III)

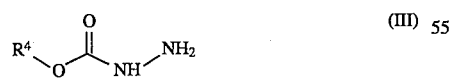

in which $R^4$ represents in each case optionally substituted alkyl, aryl or arylalkyl, —or with acid addition products of compounds of the formula (III)—if appropriate in the presence of a reaction auxiliary and if appropriate in the presence of a diluent at temperatures between −20° C. and +50° C. ("first reaction step") and the semicarbazide derivatives formed in this process of the general formula (IV)

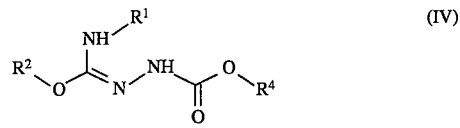

in which $R^1$, $R^2$ and $R^4$ have the abovementioned meanings,

—and/or the corresponding tautomeric compounds—are subjected to a cyclizing condensation reaction, at temperatures between 20° C. and 100° C., if appropriate after intermediate isolation, if appropriate in the presence of a base and if appropriate in the presence of a diluent ("second reaction step").

Surprisingly, the alkoxytriazolinones of the general formula (I) can be obtained in considerably higher yields by the process according to the invention than by most of the known synthetic methods.

Compared with the "diazomethane method" (F. Arndt et al, 1. c) the decisive advantage of the process according to the invention is that it can also be carried out on an industrial scale.

The especially surprising aspect is that it is virtually exclusively a mercaptan which is eliminated in the first reaction step and not an alcohol, thus allowing precise control of the reaction. In contrast to the known process, which is to be carried out at higher temperatures and in which phenol is formed as coupling product in the second reaction step—$R^4$ represents phenyl (cf. EP-A 507171, Examples II-1 and II-2)—the second step of the the process according to the invention can also be carried out in a problem-free manner with the elimination of simple alkanols, which can be recovered in a considerably more simple and less complicated fashion than in the case of phenol.

The process according to the invention therefore represents a valuable enrichment of the prior art.

The invention preferably relates to the preparation of compounds of the formula (I) in which $R^1$ represents alkyl, alkenyl or alkinyl, each of which has up to 6 carbon atoms and each of which is optionally substituted by halogen or $C_1$–$C_4$-alkoxy, or represents cycloalkyl or cycloalkylalkyl, each of which has 3 to 6 carbon atoms in the cycloalkyl moiety and, if appropriate, 1 to 4 carbon atoms in the alkyl moiety and each of which is optionally substituted by halogen or $C_1$–$C_4$-alkyl, or represents aryl or arylalkyl, each of which has 6 or 10 carbon atoms in the aryl moiety and, if appropriate, 1 to 4 carbon atoms in the alkyl moiety and each of which is optionally substituted by carboxyl, cyano, nitro, halogen, $C_1$–$C_4$-alkyl, $C_1$–$C_4$-halogenoalkyl, $C_1$–$C_4$-alkoxy, $C_1$–$C_4$-halogenoalkoxy or $C_1$–$C_4$-alkoxy-carbonyl, and $R^2$ represents alkyl, alkenyl or alkinyl, each of which has up to 6 carbon atoms and each of which is optionally substituted by halogen or $C_1$–$C_4$-alkoxy, or represents cycloalkyl or cycloalkylalkyl, each of which has 3 to 6 carbon atoms in the cycloalkyl moiety and, if appropriate, 1 to 4 carbon atoms in the alkyl moiety and each of which is optionally substituted by halogen or $C_1$–$C_4$-alkyl, or represents aryl or arylalkyl, each of which has 6 or 10 carbon atoms in the aryl moiety and, if appropriate, 1 to 4 carbon atoms in the alkyl moiety and each of which is optionally substituted by carboxyl, cyano, nitro, halogen, $C_1$–$C_4$-alkyl, $C_4$–$C_4$-halogenoalkyl, $C_1$–$C_4$-alkoxy, $C_1$–$C_4$-halogenoalkoxy or $C_1$–$C_4$-alkoxy-carbonyl.

The invention particularly relates to the preparation of compounds of the formula (I) in which $R^1$ represents methyl, ethyl, n- or i- propyl or n-, i-, s- or t-butyl, each of which is optionally substituted by fluorine, chlorine and/or bromine, methoxy or ethoxy, or represents propenyl, butenyl, propinyl or butinyl, each of which is optionally substituted by fluorine, chlorine and/or bromine, or represents cyclopropyl, cyclobutyl or cyclopropylmethyl, each of which is optionally substituted by fluorine, chlorine, methyl or ethyl, or represents phenyl or benzyl, each of which is optionally substituted by fluorine, chlorine, bromine, methyl, ethyl, trifluoromethyl, methoxy, ethoxy, difluoromethoxy, trifluoromethoxy, methoxycarbonyl or ethoxycarbonyl, and $R^2$ represents methyl, ethyl, n- or i- propyl or n-, i-, s- or t-butyl, each of which is optionally substituted by fluorine, chlorine and/or bromine, methoxy or ethoxy, or represents propenyl, butenyl, propinyl or butinyl, each of which is optionally substituted by fluorine, chlorine and/or bromine, or represents cyclopropyl, cyclobutyl or cyclopropylmethyl, each of which is optionally substituted by fluorine, chlorine, methyl or ethyl, or represents phenyl or benzyl, each of which is optionally substituted by fluorine, chlorine, bromine, methyl, ethyl, trifluoromethyl, methoxy, ethoxy, difluoromethoxy, trifluoromethoxy, methoxycarbonyl or ethoxycarbonyl.

If, for example, O,S-dimethyl methylimino-thiocarbonate and ethyl carbazinate are used as starting substances, the course of the reaction in the process according to the invention can be outlined by the following equation:

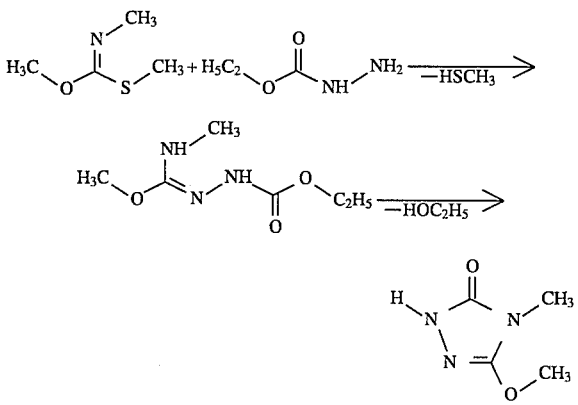

Formula (II) provides a general definition of the iminothiocarbonic diesters to be used as starting substances in the process according to the invention for the preparation of the compounds of the general formula (I). In formula (II), $R^1$ and $R^2$ preferably, or in particular, have those meanings which have already been mentioned above in connection with the description of the compounds of the formula (I) as preferred, or as particularly preferred, for $R^1$ and $R^2$; $R^3$ preferably represents $C_1$–$C_4$-alkyl which is optionally substituted by carboxyl or $C_1$–$C_4$-alkoxy-carbonyl, or represents phenyl or benzyl in particular methyl, ethyl, carboxymethyl, methoxycarbonylmethyl or ethoxycarbonylmethyl.

The starting substances of the formula (II) are known and/or can be prepared by processes known per se (cf. Chem. Ber. 120 (1987), 339–344).

Formula (III) provides a general definition of the carbazinic esters furthermore to be used as starting substances in the process according to the invention. In formula (III), $R^4$ preferably represents $C_1$–$C_4$-alkyl which is optionally substituted by $C_1$–$C_4$-alkoxy, or represents phenyl or benzyl, in particular methyl, ethyl, methoxyethyl, ethoxyethyl or phenyl.

The starting substances of the formula (III) are known chemicals for organic synthesis.

It is also advantageous to employ acid addition products of compounds of the formula (III) for carrying out the process according to the invention. Preferred addition products are those with strong protonic acids, such as, for example, hydrogen chloride ("hydrochloric acid"), hydrogen bromide, hydrogen iodide, sulphuric acid, methanesulfonic acid, benzenesulfonic acid and p-toluenesulfonic acid.

Diluents which are suitable for carrying out the process according to the invention are (for both reaction steps) the customary organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform, tetrachloromethane; ethers such as diethyl ether, diisopropyl ether, dioxane, tetrahydrofuran or ethylene glycol dimethyl ether or ethylene glycol diethyl ether; ketones such as acetone, butanone or methyl isobutyl ketone; nitriles such as acetonitrile, propionitrile or benzonitrile; amides such as N,N-dimethylformamide, N,N-dimethylacetamide, N-methylformanilide, N-methyl-pyrrolidone or hexamethylphosphoric triamide; esters such as methyl acetate or ethyl acetate, sulphoxides such as dimethyl sulphoxide, alcohols such as methanol, ethanol, n- or i-propanol, n-, i-, s- or t-butanol, ethylene glycol monomethyl ether, ethylene glycol monoethyl ether, diethylene glycol monomethyl ether, diethylene glycol monoethyl ether, as well as mixtures of these with water, or pure water.

Particularly preferred diluents are alcohols, such as methanol, ethanol or n- or i-propanol, mixtures of these with water, as well as pure water.

The first step of the process according to the invention is preferably carried out in the presence of a suitable reaction auxiliary. Suitable reaction auxiliaries are preferably protonic acids such as, for example, hydrochloric acid, sulphuric acid, phosphoric acid, carbonic acid, acetic acid, propionic acid, pivalic acid, methanesulphonic acid, benzoic acid, benzenesulphonic acid and p-toluenesulphonic acid, if appropriate also polymeric acids or acidic ion exchangers.

Particularly preferred reaction auxiliaries in the first steps of the process according to the invention are pivalic acid, acetic acid and (aqueous) hydrochloric acid.

It is also preferred to directly employ acid addition products of compounds of the formula (III).

If appropriate, the second step of the process according to the invention is carried out in the presence of a base. Suitable bases are all the conventional inorganic or organic bases. These include, for example, the hydrides, hydroxides, amides, alcoholates, acetates, carbonates or hydrogen carbonates of alkaline earth metals or alkali metals such as, for example, sodium hydride, sodium amide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, and also basic organic nitrogen compounds such as trimethylamine, triethylamine, tributylamine, N,N-dimethylaniline, N,N-dimethyl-benzylamine, pyridine, N-methylpiperidine, N,N-dimethylaminopyridine, 5-ethyl-2-methyl-pyridine, diazabicyclooctane (DABCO), diazabicyclononene (DBN) or diazabicycloundecene (DBU).

Particularly preferred as bases in the second step of the process according to the invention are alkali metal alcoholates such as sodium methylate or sodium ethylate, as well as alkali metal hydroxides such as sodium hydroxide or potassium hydroxide, in each case preferably dissolved in the appropriate alcohols or in water.

When carrying out the first step of the process according to the invention, the reaction temperatures can be varied within a substantial range. In general, the process is carried out at temperatures between −20° C. and +50° C., preferably at temperatures between −10° C. and +40° C., in particular at temperatures between 0° C. and 30° C.

When carrying out the second step of the process according to the invention, the reaction temperatures can be varied within a substantial range. In general, the process is carried out at temperatures between 20° C. and 100° C., preferably at temperatures between 30° C. and 90° C., in particular at temperatures between 40° C. and 80° C.

Both steps of the process according to the invention are generally carried out under atmospheric pressure. However, it is also possible to carry out the process under elevated or reduced pressure, in general between 0.1 bar and 10 bar.

For carrying out the process according to the invention for the preparation of the compounds of the formula (I), 0.5 to 1.2 tool, preferably 0.8 to 1.1 tool, of carbazinic ester of the formula (III) and, if appropriate, 0.001 to 2.0 mol, preferably 0.01 to 1.0 tool, of reaction auxiliary are generally employed per mole of iminothiocarbonic diester of the formula (II).

In a preferred embodiment of the process according to the invention, the starting substances of the formula (II) and of the formula (III)—if appropriate, the acid addition products of the latter—and, if appropriate, a reaction auxiliary are mixed in a suitable diluent and stirred at the temperature required until virtually no starting material is present. The intermediate of the formula (IV) can then be isolated in the customary manner, for example by concentrating the mixture, digesting the residue with an organic solvent, such as, for example, diethyl ether, methyl t-butyl ether or ethyl acetate, and filtering with suction. Alternatively, the intermediate of the formula (IV) can be treated with a base—if appropriate dissolved in one of the abovementioned diluents—and the mixture stirred at the temperature required for cyclizing condensation until the reaction has ended, without intermediate isolation.

Working-up to isolate the products of the formula (I) can be effected by customary methods. For example, the mixture is concentrated, the product is taken up in water, and the mixture is neutralized or acidified, for example using hydrochloric acid. If the product is obtained as crystals in this process, it is isolated by filtration with suction. If not, it is shaken with an organic solvent which is virtually immiscible with water, such as, for example, ethyl acetate, and the organic phase is dried—for example using magnesium sulphate—and filtered. After the solvent has been removed carefully by distillation under reduced pressure, the product of the formula (I) is then obtained as a residue. The crude products can be purified by recrystallization, stirring with a suitable organic solvent, such as, for example, petroleum ether, or by distillation.

The compounds of the formula (I) to be prepared by the process according to the invention can be used as intermediates for the preparation of herbicidally active compounds (cf. EP-A 477646 and EP-A 507171).

PREPARATION EXAMPLES

Example 1

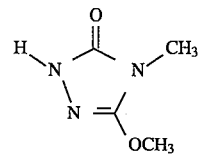

12 g (85 mmol) of ethyl carbazinate hydrochloride are introduced into methanol at 0° C. to 5° C., and a solution of 10.5 g (88 mmol) of O,S-dimethyl methyl iminothiocarbonate in 15 ml of methanol is added dropwise at this temperature. The mixture is stirred for 3 hours at 0° C. to 5° C., and the methylmercaptan which is formed as coupling product is expelled using nitrogen. 15.5 g of a solution of sodium methanolate in methanol (86 mmol of NaOCH$_3$) are subsequently added dropwise at 0° C. to 5° C., and the reaction mixture is stirred for 30 minutes at approximately 5° C., for a further 30 minutes at approximately 20° C., and—after a further 15.5 g of the abovementioned sodium methanolate solution have been added—for a further 6 hours at 50° C. It is then concentrated under a water pump vacuum, the residue is taken up in 60 ml of saturated sodium chloride solution, the mixture is acidified using 20% strength hydrochloric acid with ice-cooling, and the product obtained as crystals is isolated by filtration with suction. The resulting salt-containing product is dissolved in 25 ml of hot water and then stirred for 4 hours at 20° C. and refiltered with suction.

9.9 g of 5-methoxy-4-methyl-2,4-dihydro-3H- 1,2,4-triazol-3-one (83% pure, remainder: sodium chloride) are obtained; yield: 74.5% of theory.

Example 2

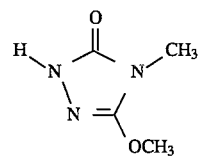

21.4 g (0.20 mol) of ethyl carbazinate and 2.2 g (0.02 mol) of ethyl carbazinate hydrochloride are introduced into 80 ml of methanol, and 29.3 g (0.24 mmol) of O,S-dimethyl methyl iminothiocarbonate are added. The mixture is then stirred for 4 hours at 20° C. 43 g of a solution of sodium methanolate in methanol (0.24 mmol of NaOCH$_3$) are subsequently added, and the reaction mixture is stirred for 7 hours at 60° C. For working-up, the mixture is concentrated, the residue is taken up in 95 ml of water, and the mixture is neutralized using concentrated hydrochloric acid with ice-cooling. The product obtained as crystals is isolated by filtration with suction.

21.7 g (70% of theory) of 5-methoxy-4-methyl-2,4-dihydro-3H-1,2,4-triazol-3-one of melting point 148° C. are obtained.

Example 3

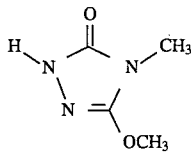

21.4 g (0.20 mol) of ethyl carbazinate are introduced into 70 ml of water and 4 g of concentrated hydrochloric acid (0.04 mmol of HCl) are added at approximately 5° C. 26.6 g (0.22 mmol) of O,S-dimethyl methyliminothiocarbonate are then added. The mixture is then stirred for 4 hours at 5° C. 21.3 g of a 45% strength solution of sodium hydroxide in water (0.24 mmol of NaOH) are subsequently added, and the reaction mixture is stirred for 4 hours at 55° C. to 60° C. For working-up, the mixture is neutralized using concentrated hydrochloric acid with ice-cooling. The product obtained as crystals is isolated by filtration with suction.

23.2 g (89% of theory) of 5-methoxy-4-methyl-2,4-dihydro-3H-1,2,4-triazol-3-one of melting point 148° C. are obtained.

Example 4

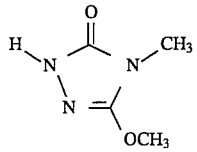

6.7 g (0.03 mmol) of phenyl N'-(α-methylamino-α-methoxy-methylene)-hydrazine-N-carboxylate are introduced into a mixture of ethanol and 48 ml of 3N sodium hydroxide solution at 0° C., and the reaction mixture is stirred for a further hour at 0° C. Ice is then added, and the mixture is acidified using concentrated hydrochloric acid and saturated with sodium chloride. The reaction product is extracted using ethyl acetate, and the organic phase is dried using sodium sulphate and filtered. The filtrate is concentrated, the residue is stirred with diisopropyl ether, and the product which has been obtained as crystals is isolated by filtration with suction.

3.1 g (80% of theory) of 5-methoxy-4-methyl-2,4-dihydro-3H-1,2,4-triazol-3-one of melting point 148° C. are obtained.

Example 5

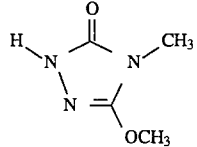

21.2 g (0.2 mol) of ethyl carbazinate are introduced into 40 ml of water, and 4.0 g of concentrated hydrochloric acid (0.04 mmol of HCl) are added dropwise at 0° C. A solution of 26.2 g (0.22 mmol) of O,S-dimethyl methyliminocarbonate in 30 ml of methanol is then added dropwise at 0° C. The reaction mixture is stirred for 17 hours in an ice-bath, and the methylmercaptan formed as coupling product is expelled using nitrogen. 21.3 g of 45% strength aqueous sodium hydroxide solution (0.24 mmol of NaOH) are subsequently added dropwise, and the mixture is then heated for 3 hours at 55° C. After cooling, the methanol is distilled off under a water pump vacuum, the residue is diluted with 90 ml of water, and the mixture is neutralized by adding concentrated hydrochloric acid, in an ice-bath. The product obtained as crystals is isolated by filtration with suction.

24 g of 5-methoxy-4-methyl-2,4-dihydro-3H-1,2,4-triazol-3-one (95.2% pure, yield: 89% of theory) are obtained.

Example 6

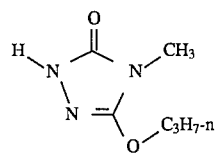

21.1 g (0.2 mol) of ethyl carbazinate are introduced into 70 ml of water, 4 g of concentrated hydrochloric acid (0.04 mol of HCl) are added, and the mixture is then cooled to 0° C. 32.9 g (0.22 mmol) of O-n-propyl S-methyl methyliminothiocarbonate are then added dropwise, and the mixture is stirred for a further 15 hours with ice-cooling, the methylmercaptan which has formed as coupling product being expelled using nitrogen. 21.3 g of 45% strength sodium hydroxide solution (0.22 mmol of NaOH) are subsequently added at 20° C., and the mixture is heated for 6 hours at 60° C.

The mixture is then neutralized by adding concentrated hydrochloric acid with ice-cooling and extracted three times using in each case 100 ml of ethyl acetate. The combined extraction solutions are dried using sodium sulphate and filtered. The filtrate is concentrated under a water pump vacuum, the residue is stirred with petroleum ether, and the product, which is obtained as crystals, is isolated by filtration with suction. 26.7 g (84% of theory) of 5-n-propyl-4-methyl-2,4-dihydro-3H-1,2,4-triazol-3-one of melting point 77° C. are obtained.

Example 7

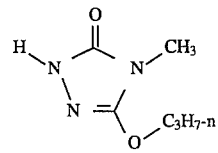

21.2 g (0.2 mmol) of ethyl carbazinate are introduced into 40 ml of water, and 4 g of concentrated hydrochloric acid (0.04 mmol of HCl) are added dropwise at 0° C. A solution of 33.8 g (0.22 mmol) of O-n-propyl S-methyl methyliminothiocarbonate in 30 ml of methanol is then added dropwise at 0° C. in the course of 50 minutes, and the mixture is stirred for a further 6 hours at 0° C. and another 15 hours at 20° C., the methyl mercaptan which is formed as coupling product being expelled using nitrogen. 21.3 g of 45% strength aqueous sodium hydroxide solution (0.24 mmol of NaOH) are then added dropwise, and the mixture is stirred for 6 hours at 55° C. to 60° C. It is subsequently concentrated under a water pump vacuum and the residue neutralized using concentrated hydrochloric acid. The mixture is extracted three times using in each case 100 ml of ethyl acetate, and the combined extraction solutions are dried using sodium sulphate and filtered. The filtrate is concentrated, the residue triturated with petroleum ether and the product, which is obtained as crystals, isolated by filtration with suction.

29.7 g (92% of theory) of 5-n-propoxy-4-methyl-2,4-dihydro-3H-1,2,4-triazol-3one of melting point 77° C. are obtained.

Example 8

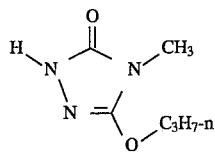

A mixture of 95.5 g i0.5 mmol) of O-n-propyl S-(2-methoxylethyl) methyliminothiocarbonate, 76 g (0.5 mmol) of phenyl carbazinate and 47 g (0.5 mol) of phenol is stirred for 10 hours at 20° C. and a further 3 hours at 60° C. It is then concentrated and distilled at 1 mbar 47.5 g of a crude distillate, of which 79.2% are the desired 5-n-propoxy-4-methyl-2,4-dihydro-3H-1,2,4-triazol-3-one are obtained (yield: 47.9% of theory).

Example 9

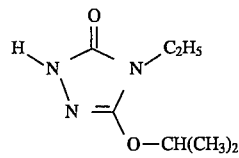

Analogously to Example 3, by reacting ethyl carbazinate and O-isopropyl S-methyl ethyliminocarbonate (excess of 10 mol-%) in the presence of pivalic acid (50 mol-%, instead of 20% mmol-% of HCl) and further reacting the intermediate thereby formed with NaOCH₃ (instead of NaOH) there is obtained 4-ethyl-5-isopropoxy-2,4-dihydro-3H-1,2,4-triazol-3-one (yield: 62% of theory) of m.p. 69°–70° C. (after distillation).

Example 10

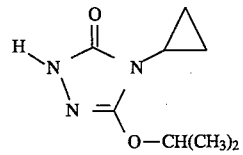

Analogously to Examples 3 and 9 but employing 100 mol-% of pivalic acid, there is obtained 4-cyclopropyl-5-isopropoxy-2,4-dihydro-3H-1,2,4-triazol-3-one (yield: 64% of theory) of m.p. 146°–147° C. (recrystallized from water). Intermediates of the Formula (IV)

Example (IV-1 )

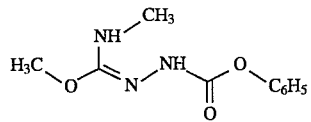

5.66 g (0.03 mol) of phenyl carbazinate hydrochloride are introduced into 50 ml of methanol, and, after cooling to 0° C. to 5° C., 4.24 g (0.035 mol) of O,S-dimethyl methyliminothiocarbonate are added. The mixture is stirred for 2 hours at 0° C. to 5° C., and the methylmercaptan formed as coupling product is expelled using nitrogen. 3.04 g (0.03 mol) of triethylamine are then added dropwise at 0° C., and the mixture is subsequently concentrated under a water pump vacuum. The residue is stirred with a small amount of water and the crystalline product isolated by filtration with suction.

5.5 g (82% of theory) of phenyl N'-(α-methylamino-α-methoxy-methylene)- hydrazine-N-carboxylate of melting point 129° C. (with decomposition) are obtained.

Example (IV-2)

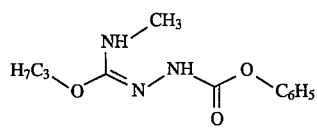

20.0 g (0.106 mol) of phenyl carbazinate hydrochloride are introduced into 200 ml of methanol and, after cooling to 0° C. to 5° C., 16.3 g (0.106 mol) of O-propyl S-methyl methyliminothiocarbonate are added. The mixture is stirred for 4 hours at 0° C. to 5° C. and the methylmercaptan formed as coupling product expelled using nitrogen. 10.8 g (0.106 mmol) of triethylamine are then added dropwise at 0° C. to 5° C., and the mixture is subsequently concentrated under a water pump vacuum. The residue is stirred with 300 ml of ethyl acetate and subjected to filtration with suction, the mother liquor is concentrated, the residue which remains is stirred with petroleum ether, and the product obtained as crystals is isolated by filtration with suction.

24.5 g (92% of theory) of phenyl N'-(α-methylamino-α-propoxy-methylene)-hydrazine-N-carboxylate are obtained.

Example (IV-3)

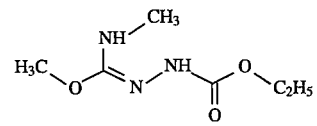

12.0 g (85 mmol) of ethyl carbazinate hydrochloride are introduced into 120 ml of methanol, and 10.5 g (88 mmol) of O,S-dimethyl methyliminothiocarbonate are added at 0° to 5° C. The mixture is stirred for 2 hours at 0° C. and the methylmercaptan formed as coupling product is expelled using nitrogen. 7.22 g (86 mmol) of sodium hydrogen carbonate are then added at 5° C., and, after the mixture has been stirred for two hours, it is subjected to filtration with suction. The filtrate is concentrated under a water pump vacuum, the residue stirred with 200 ml of ethyl acetate and the product obtained as crystals isolated by filtration with suction.

11.95 g (80% of theory) of ethyl N'-(α-methylamino-α-methoxy-methylene)- hydrazine-N-carboxylate of melting point 128° C. are obtained.

Example (IV-4)

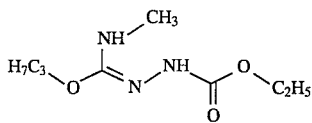

35.0 g (0.25 mol) of ethyl carbazinate hydrochloride are introduced into 500 ml of methanol and, after cooling to 0° C., 38.7 g (0.25 mmol) of O-propyl S-methyl methyliminothiocarbonate are added. The mixture is stirred for 2.5 hours at 5° C. and the methylmercaptan formed as coupling product is expelled using nitrogen. 34.75 ml (0.25 mmol) of triethylamine are then added dropwise at 0° C. and, after 20 minutes, the mixture is concentrated under a water pump vacuum. The residue is stirred with 300 ml of acetone and subjected to filtration with suction, the filtrate is concentrated, the residue stirred with 300 ml of petroleum ether and the product obtained as crystals isolated by filtration with suction.

45.9 g (91% of theory) of ethyl N'-(α-methylamino-α-propoxy metehylene)-hydrazine-N-carboxylate of melting point 104° C. are obtained.

Example (IV-5)

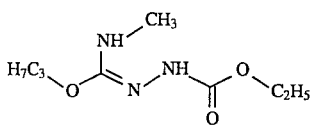

58.9 g (0.192 mmol) of ethyl carbazinate dihydrogensulphate are introduced into 350 ml of methanol and, after cooling to 0° C. to 5° C., 60.35 g (0.39 mol) of O-propyl S-methyl methyliminothiocarbonate are added. The mixture is stirred for 3 hours at 0° C. to 5° C., and the methylmercaptan formed as coupling product is expelled using nitrogen. 32.76 g (0.39 mol) of sodium hydrogen carbonate are then added at 0° C. to 5° C. and, after 30 minutes at 0° C. to 5° C. and two further hours at 20° C., the mixture is subjected to filtration over kieselguhr and the solvent carefully removed from the filtrate by distillation under reduced pressure.

73.5 g (94% of theory) of ethyl N'-(α-methylamino-α-propoxy-methylene)-hydrazine-N-carboxylate of melting point 104° C. are obtained.

We claim:

1. A process for the preparation of an alkoxytriazolinone of the formula

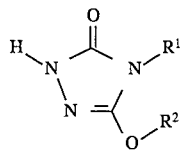

in which $R^1$ is optionally halogen or $C_1$–$C_4$-alkoxy substituted alkyl, alkenyl or alkinyl wherein each of said groups has up to 6 carbon atoms, optionally halogen or $C_1$–$C_4$-alkyl substituted $C_3$–$C_6$-cycloalkyl, optionally halogen or $C_1$–$C_4$ alkyl substituted $C_3$–$C_4$-cycloalkyl-$C_1$–$C_4$-alkyl, optionally substituted $C_6$–$C_{10}$-aryl, or optionally substituted $C_6$–$C_{10}$-aryl-$C_1$–$C_4$-alkyl wherein said substituents are selected from the group consisting of carboxyl, cyano, nitro, halogen, $C_1$–$C_4$-alkyl, $C_1$–$C_4$-halogenoalkyl, $C_1$–$C_4$-alkoxy, $C_1$–$C_4$-halogenoalkoxy and $C_1$–$C_4$-alkoxy-carbonyl, and $R^2$ is optionally halogen or $C_1$–$C_4$-alkoxy, substituted alkyl, alkenyl or alkinyl wherein each of said groups has up to 6 carbon atoms, optionally halogen or $C_1$–$C_4$-alkyl substituted $C_3$–$C_6$-cycloalkyl, optionally halogen or $C_1$–$C_4$ alkyl substituted $C_3$–$C_4$-cycloalkyl-$C_1$–$C_4$-alkyl, optionally substituted $C_6$–$C_{10}$-aryl, or optionally substituted $C_6$–$C_{10}$-aryl-$C_1$–$C_4$-alkyl wherein said substituents are selected from the group consisting of carboxyl, cyano, nitro, halogen, $C_1$–$C_4$-alkyl, $C_1$–$C_4$-halogenoalkyl, $C_1$–$C_4$-alkoxy, $C_1$–$C_4$-halogenoalkoxy and $C_1$–$C_4$-alkoxy-carbonyl, which comprises (1) reacting an iminothiocarbonic diester of the formula

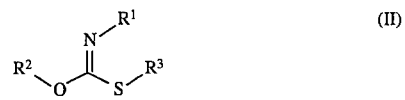

in which $R^1$ and $R^2$ have the abovementioned meanings and $R^3$ is $C_1$–$C_4$-alkyl which is optionally substituted by carboxyl or $C_1$–$C_4$-alkoxy-carbonyl or is phenyl; or benzyl, with a carbazinic ester of the formula

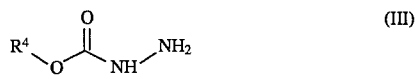

in which $R^4$ is $C_1$–$C_4$-alkyl which is optionally substituted by $C_1$–$C_4$-alkoxy, or is phenyl or benzyl, or an acid addition product thereof optionally in the presence of a protic acid a polymeric acid, or an acid ion exchanger and a diluent and at a temperature between –20° C. and +50° C.; and (2) cyclizing the semicarbazide derivative of the formula

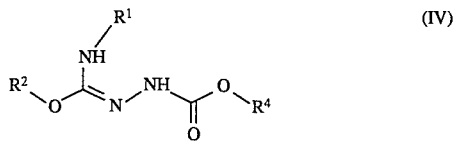

in which $R^1$, $R^2$ and $R^4$ have the abovementioned meanings, or its corresponding tautomer which is formed in step (1) at a temperature between 20° C. and 100° C., optionally in the presence of a base and a diluent and optionally isolating said intermediate before performing the cyclization step.

2. The process according to claim 1, wherein the first reaction step is carried out at a temperature between –10° C. and +40° C.

3. The process according to claim 1, wherein the first reaction step is carried out at a temperature range between 0° C. and 30° C.

4. The process according to claim 1, wherein the second reaction step is carried out at a temperature between 30° C. and 90° C.

5. The process according to claim 1, wherein the second step is carried out between 40° C. and 80° C.

6. The process according to claim 1, wherein the iminothiocarbonic diester employed is O,S-dimethyl methyliminothiocarbonate, O-n-propyl S-methyl methyliminothiocarbonate or O-n-propyl S-(2-methoxyethyl) iminothiocarbonate.

7. The process according to claim 1, wherein the carbonic ester employed is ethyl carbazinate, phenyl carbazinate or their hydrochlorides or dihydrogen sulphates.

8. The process according to claim 1, wherein the diluent in both reaction steps is an alcohol, an alcohol/water mixture or water.

9. The process according to claim 1, wherein the protic acid is pivalic acid, acetic acid or aqueous hydrochloric acid.

10. The process according to claim 1, wherein the base is an alkali metal alcoholate or alkali metal hydroxide optionally dissolved in alcohol or in water.

* * * * *

UNITED STATES PATENT AND TRADEMARK OFFICE
CERTIFICATE OF CORRECTION

PATENT NO. : 5,606,070
DATED      : February 25, 1997
INVENTOR(S): Wroblowsky, et al.

It is certified that error appears in the above-indentified patent and that said Letters Patent is hereby corrected as shown below:

Col. 12, line 5    After " $C_1-C_4$-alkoxy " delete " , " (comma)

Signed and Sealed this

Tenth Day of June, 1997

Attest:

Attesting Officer

BRUCE LEHMAN

Commissioner of Patents and Trademarks